(12) United States Patent
Hadcock et al.

(10) Patent No.: US 8,610,899 B2
(45) Date of Patent: Dec. 17, 2013

(54) ROTATIONAL AND LINEAR SYSTEM AND METHODS FOR SCANNING OF OBJECTS

(75) Inventors: Kyle J. Hadcock, Webster, NY (US); Stephen Heveron-Smith, Webster, NY (US); Vincent Lamanna, Ontario, NY (US); David Baranson, Encinitas, CA (US)

(73) Assignee: Lumetrics, Inc., Rochester, NY (US)

( * ) Notice: Subject to any disclaimer, the term of this patent is extended or adjusted under 35 U.S.C. 154(b) by 142 days.

(21) Appl. No.: 12/958,532

(22) Filed: Dec. 2, 2010

(65) Prior Publication Data

US 2011/0128552 A1 Jun. 2, 2011

Related U.S. Application Data

(60) Provisional application No. 61/265,921, filed on Dec. 2, 2009.

(51) Int. Cl.
*G01B 11/02* (2006.01)
*G01L 1/24* (2006.01)

(52) U.S. Cl.
USPC .......................................... 356/496; 356/35.5

(58) Field of Classification Search
USPC ......... 356/450, 455, 456, 462, 489, 492, 495, 356/496, 511, 457
See application file for complete search history.

(56) References Cited

U.S. PATENT DOCUMENTS

| | | | |
|---|---|---|---|
| 5,659,392 A | 8/1997 | Marcus et al. | |
| 5,864,778 A | 1/1999 | Morcom et al. | |
| 6,034,772 A | 3/2000 | Marcus et al. | |
| 6,067,161 A | 5/2000 | Marcus et al. | |
| 7,456,973 B2 * | 11/2008 | Steinbichler et al. | 356/457 |
| 7,578,165 B1 * | 8/2009 | Stupecky | 73/1.81 |
| 2001/0040682 A1 * | 11/2001 | Lindsay et al. | 356/520 |
| 2010/0265516 A1 * | 10/2010 | De Groot et al. | 356/511 |

OTHER PUBLICATIONS

Medical applications web page of Lumetrics Inc., published 2008 or earlier, reproduced using Internet Archive website www.archive.org/.
Medical balloon catheter measurement product brochure of Lumetrics Inc., published 2008 or earlier.
Tubing measurement product brochure of Lumetrics Inc., published 2006.
OptiGage(TM) product brochure of Lumetrics Inc., published 2006.
Marketing presentation of Lumetrics Inc., published 2006.

* cited by examiner

*Primary Examiner* — Gregory J Toatley
*Assistant Examiner* — Hina F. Ayub
(74) *Attorney, Agent, or Firm* — Patent Innovations LLC; John M. Hammond

(57) ABSTRACT

A scanning system comprised of a multi-axis drive module comprised of a first linear drive operable along a first axis, a second linear drive joined to the first linear drive and operable along a second axis non-parallel to the first axis, and a first rotary drive mounted on the second linear drive, operable around an axis parallel to the first axis, and comprised of a rotary fixture for holding the object. A first optical probe is provided for scanning the object. The rotary fixture for holding the object may include a central object-receiving port. A first fluid circuit may be provided, which is in communication with the central object-receiving port. In that manner, an internal cavity of the object may be pressurized through a passageway in the portion of the object that is disposed in the central object-receiving port, thereby stabilizing a region of the object to be scanned.

27 Claims, 16 Drawing Sheets

ROTATIONAL AND LINEAR SYSTEM AND METHODS FOR SCANNING OF OBJECTS

CROSS-REFERENCE TO RELATED PATENT APPLICATIONS

This application claims priority from U.S. provisional patent Application No. 61/265,921 filed Dec. 2, 2009, the disclosure of which is incorporated herein by reference.

BACKGROUND

1. Technical Field

This invention relates to scanning measurement systems which scan an object linearly and rotationally, particularly to optical scanning measurement systems, and in certain embodiments, to interferometric scanning measurement systems.

2. Description of Related Art

In many fields of manufacturing, the level of precision to which products can be made is continually advancing. There are many products which are axially symmetric, or nearly so, and which are made to exacting standards due to the particular applications of the products. Additionally, these axially symmetric products may be comprised of multiple layers or thin films of varying thicknesses and physical properties.

One example of such a product is the balloon catheter, which is used in balloon angioplasty medical procedures to open sclerotic arteries. Not surprisingly, in order to be safe and effective in such a procedure, a balloon catheter must satisfy a broad range of specifications. This is needed in order to obtain FDA approval for the catheter device and for operation of the catheter device manufacturing plant, as well as to minimize product liability of the manufacturing company. Wall thickness specifications for a balloon catheter are particularly important.

Whenever there is a product specification, there is a need to measure the product to confirm that it is meeting the specification. For an invasive medical device such as a balloon catheter, where a patient's life is at risk in the event of a product failure, it is required that every individual catheter be measured to determine that it meets specifications. It is undesirable that a sample of a production lot of catheters be measured, and then the full lot be deemed satisfactory. Thus, any measurement of catheter properties must be non-destructive and non-contact. Additionally, the measurement itself must be sufficiently reliable so as to have substantially no risk of mistakenly finding a defective catheter to be within specifications and releasing it for use in a patient, when it should be rejected and discarded. The measurement must also be sufficiently fast so as to enable the desired manufacturing throughput, in order for the overall catheter manufacturing process to be economically viable.

Scanning methods and apparatus which use an optical probe may be particularly effective in making wall thickness, diameter, and length measurements of balloon catheters, as well as various other high precision and/or multilayer axially symmetric products. Optical probe-based measurements are non-destructive, non-contact, highly precise, and fast. One particular optical probe-based measurement uses the principles of low coherence interferometry, wherein an optical probe directs low coherence light through a transparent, translucent or colored object. Reflected light is received back by the probe and transmitted to a signal converter and a computer. Software programs in the computer analyze the reflected light signals and determine dimensional and layer thickness(es) of the object. For further details on this measurement apparatus and methods, one may refer to U.S. Pat. Nos. 5,596,409, 5,659,392, 6,034,772, 6,034,774, 6,038,027, 6,067,161, 6,522,410, 6,724,487, all of Marcus et al.; and U.S. Pat. No. 7,206,076 of Blalock. The disclosures of these United States patents are incorporated herein by reference in their entireties.

A measurement product which employs low coherence interferometry is the OptiGauge™, which is manufactured and sold by Lumetrics, Inc. of West Henrietta, N.Y. This product meets the non-destructive, non-contact, and precision requirements for making measurements of balloon catheters and other similar high precision products made according to stringent specifications. Such capabilities notwithstanding, there has remained a need for an optical probe-based measurement system, whether it uses an interferometric probe, or another optical probe, wherein the system can perform a full scan along the length and around the circumference of an axially symmetric product. There is a need for such a system to have the capability to scan a product which has variation in diameter along its length. For balloon catheters and other objects having an internal cavity and a flexible wall, there is a need to stabilize the position of the flexible wall surface while making the measurements.

There is a further need for a system which can be programmed to perform an entire scan of the product automatically according to a computer program, acquire the thickness and diameter data of an array of axial and circumferential locations along the product, compare the data to product specifications, and to indicate whether the product is acceptable or rejected.

SUMMARY

The present invention meets these needs by providing a system for scanning an object, and methods of using the system. The system is particularly suited to scanning objects linearly and rotationally, so as to scan substantial portions of the object. The system is particularly suited to scanning objects that are axially symmetric, and that have an internal cavity and a flexible wall. The system may be used to make scanning measurements of wall thicknesses, coated layer thicknesses, outside diameter, ovality, and concentricity of objects, as well as inside diameter of hollow objects.

In one aspect, the problem of scanning an object having axial symmetry is solved by a scanning system comprising means for gripping the object, means for pressurizing an internal cavity of the object to stabilize a first region of the object, a first probe, and means for scanning the first probe linearly and circumferentially relative to the first region of the object. The system may further comprise a second probe, and means for scanning the second probe circumferentially relative to the second region of the object. The system may further comprise means for varying the pressure provided to the internal cavity of the object.

In one embodiment, a scanning system in accordance with the invention is comprised of a multi-axis drive module comprised of a first linear drive operable along a first axis, a second linear drive joined to the first linear drive and operable along a second axis non-parallel to the first axis, and a first rotary drive mounted on the second linear drive, operable around an axis parallel to the first axis, and comprised of a rotary fixture for holding the object. A first interferometric optical probe is provided for axially scanning along the object in a direction parallel to the first axis. When the object is held by the rotary fixture, it may be rotated while the first probe is scanned along the object in the direction of the first axis. In that manner, the object is linearly and rotationally scanned by the system.

The first probe may be mounted on a first support structure, such that it is held stationary, while the multi-axis drive module drives the object linearly and rotationally along the first probe to linearly and rotationally scan the object. The first probe may be an optical probe, and in particular, an interferometric probe.

The rotary fixture for holding the object may include a central object-receiving port. A first fluid circuit may be provided, which is in communication with the central object-receiving port of the rotary fixture. In that manner, an internal cavity of the object may be pressurized through a passageway in the portion of the object that is disposed in the central object-receiving port. This feature is particularly useful for inflating a balloon catheter object during the scanning process, so as to provide a taut, uniform surface for scanning.

The rotary fixture may be further comprised of a gripper for gripping the object so that it is rotatable around its central axis. The gripper may be electrically actuated, or fluid actuated by a second fluid circuit, i.e. hydraulically (liquid pressure) actuated, or pneumatically (gas, e.g., air) actuated.

The system may be further comprised of a second probe mounted on the base and alignable with at least a portion of the object to be scanned. This feature is particularly useful for scanning the conically tapered end regions of a balloon catheter object.

In another embodiment, a scanning system in accordance with the invention is comprised of a rotatable fixture comprised of a collet having a central port for receiving a portion of the object; a first fluid circuit in communication with may be further comprised of a fluid pressure actuated gripper, with the system being further comprised of a second fluid circuit in communication with the fluid pressure actuated gripper. The system may include a multi-axis drive module comprised of a first linear drive operable along a first axis, a second linear drive joined to the first linear drive and operable along a second axis non-parallel to the first axis, and a first rotary drive mounted on the second linear drive, operable around an axis parallel to the first axis, and operably connected to the rotatable fixture. The first probe may be an optical probe, such as, e.g., interferometric probe.

In accordance with the invention, there is further provided a method of scanning an object with a scanning system. The method comprises gripping the object, applying fluid pressure to an internal cavity of the object to stabilize a first region of the object, and scanning a first portion of the first region of the object with a first probe. The method may further comprise rotating the object, and scanning the first probe along a second portion of the first region of the object. Alternatively or additionally, the method may further comprise rotating the object, and scanning a second probe along a first portion of a second region of the object.

The system may include a computer for controlling components thereof, with the method further comprising entering a linear and rotational scanning program into the system computer, uploading the scanning program to the multi-axis controller of the system, and executing the scanning program. The program may include a scanning routines for the first probe, and the second probe. The program may include scanning routines for additional probes. The method may include performing a sequence of scans at different fluid pressures provided to the cavity of the object. The method may include acquiring and storing the scan data from the probe(s), analyzing the data, and/or displaying the data on a screen, paper, or other device, and/or indicating acceptance or rejection of the object based on one or more criteria.

BRIEF DESCRIPTION OF THE DRAWINGS

The present disclosure will be provided with reference to the following drawings, in which like numerals refer to like elements, and in which.

Figure 1:
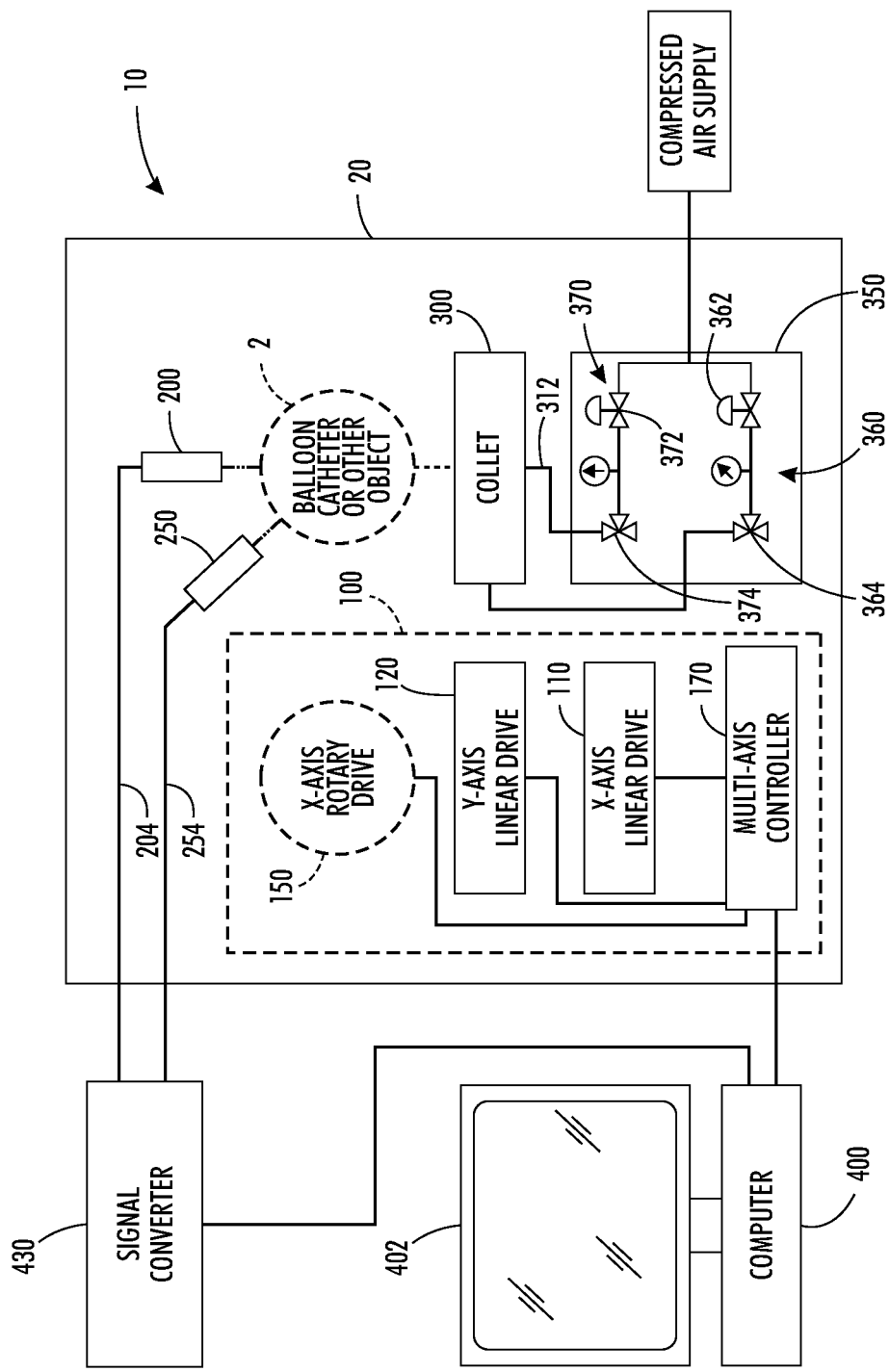
FIG. 1 is a block diagram of a rotational and linear scanning system of the present invention.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used throughout to designate identical elements. In the following disclosure, the present invention is described in the context of its use as a system for scanning balloon catheters. However, it is not to be construed as being limited only to use in such an application. The invention is adaptable to any use in which it is desirable to make scanning measurements of an object that is axially symmetric.

Embodiments of the present invention are also described wherein the system probes are optical probes, and in particular, interferometric probes. However, the present invention is not limited to use with only such probes. Other optical probes may be used in the instant scanning systems, such as a chromatic aberration probe, a confocal probe, a laser micrometer, and/or a camera. Additionally, other non-optical probes may be used with the instant scanning system, including but not limited to ultrasonic probes, and linear variable displacement transformers (LVDTs).

The system is also not limited solely to making dimensional measurements of objects, such as object diameter and object wall and/or film thicknesses. The system may be used for other scanning applications, including but not limited to surface inspections, surface mapping, and surface image acquisition; and where the signal from the probe penetrates the bulk of the object, and/or where the probe can detect a signal from the bulk of the object, bulk properties of the object as a function of scanned location may be obtained.

Additionally, the following description identifies certain components with the adjectives "front," "rear," "top," "upper," "bottom," "lower," "left," "right," etc. These adjectives are provided in the context of use of the system for scanning balloon catheters, and in the context of the orientation of the system in the drawings. The description is not to be construed as limiting the scanning system to use in a particular spatial orientation. The instant system may be used in orientations other than those shown and described herein.

In describing the present invention, a variety of terms are used. As used herein, the term "optical probe" is meant to indicate any probe which emits to an object and/or receives from an object photonic energy of any wavelength or wavelengths when performing a scanning operation of the object. Additionally, it is noted that in FIGS. 2-9, the scanning system is shown without a rotary collet, a first probe, a second probe and probe fixture, or an object to be scanned being present. FIGS. 11-14 show these features of the system.

FIG. 1 is a block diagram of one embodiment of a rotational and linear scanning system of the present invention. The scanning system 10 is comprised of a base 20, a multi-axis drive module 100 disposed on the base 20, and a first probe 200 that is axially scannable along an object to be scanned, such as a balloon catheter 2. The multi-axis drive module 100 is a means for scanning first and second probes linearly and circumferentially relative to regions of the object, and is comprised of a first linear drive 110 linearly drivable along a first axis, a second linear drive 120 joined to the first linear drive 110 and linearly drivable along a second axis non-parallel to the first axis, and a first rotary drive 150 mounted on the second linear drive 120. The multi-axis drive module 100 may also include a multi-axis controller 170 in signal communication with the drives 110, 120, and 150. The system 10 may be further comprised of a computer 400 in signal communication with the multi-axis drive module 100 and with the first probe 200. The system 10 may further include a signal converter 430 in signal communication with the computer 400 and with the first probe 200. The rotary drive 150 may include a rotary collet 300 comprising a central object-receiving port and a gripper for gripping the object so that it is rotatable around a central axis by the rotary collet 300. The gripper may be electrically actuated, or fluid actuated, i.e. hydraulically (liquid pressure) actuated, or pneumatically (gas, e.g., air) actuated.

In an embodiment comprising a pneumatically actuated collet gripper, the system may be further comprised of a pneumatic module 350 comprising a first pneumatic circuit 370 in communication with the central object-receiving port of the rotary collet 300, and a second pneumatic circuit 360 in communication with the pneumatic gripper. (It will be apparent to those of skill in the art that the pneumatic gripper may and pneumatic module may instead be a hydraulic gripper and hydraulic module, i.e. operated by liquid pressure.) These and other features of the scanning system 10 will now be described with reference to FIGS. 2-15.

Figure 2:
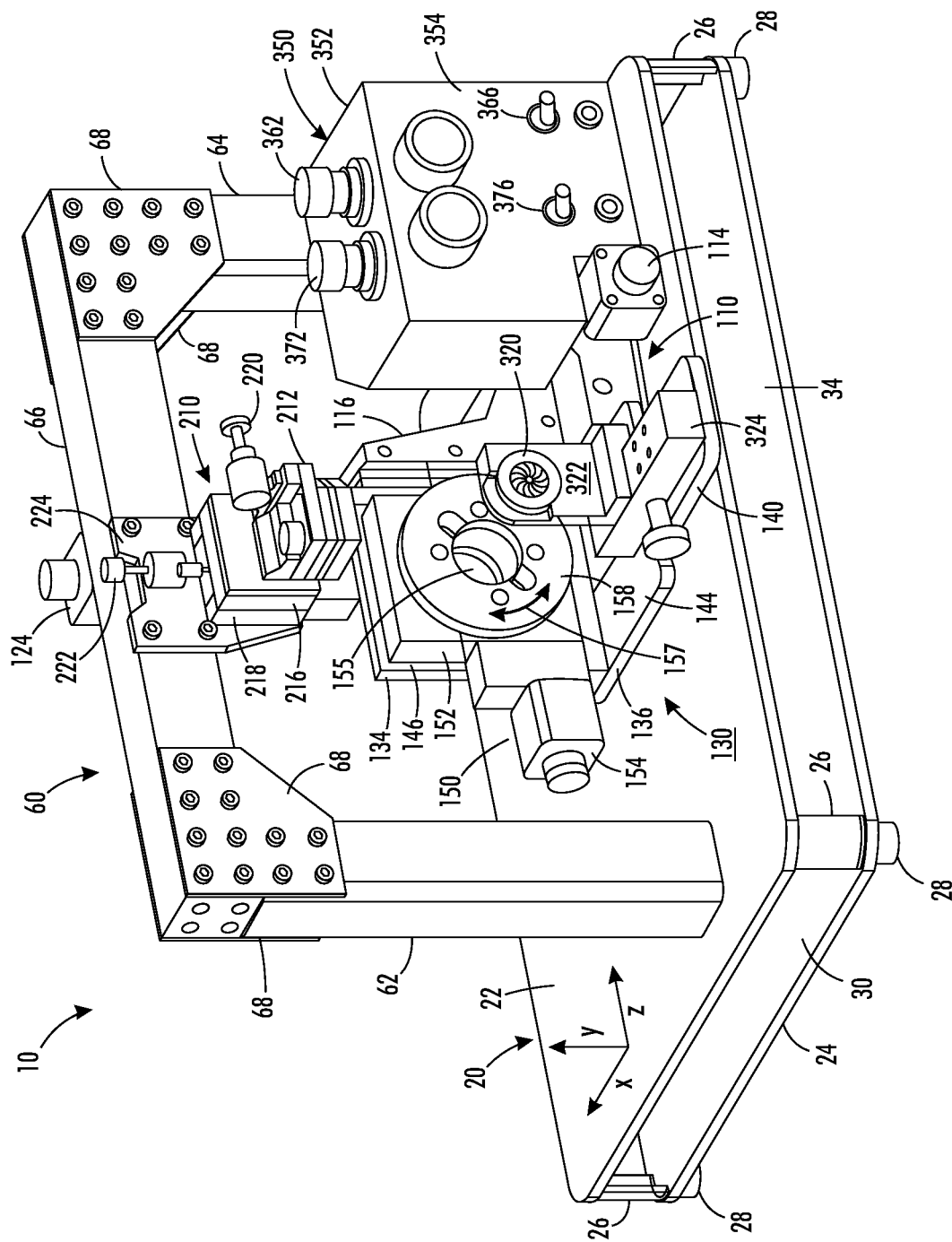
FIG. 2 is a front perspective view of one embodiment of the rotational and linear scanning system of the present invention.
Figure 3:
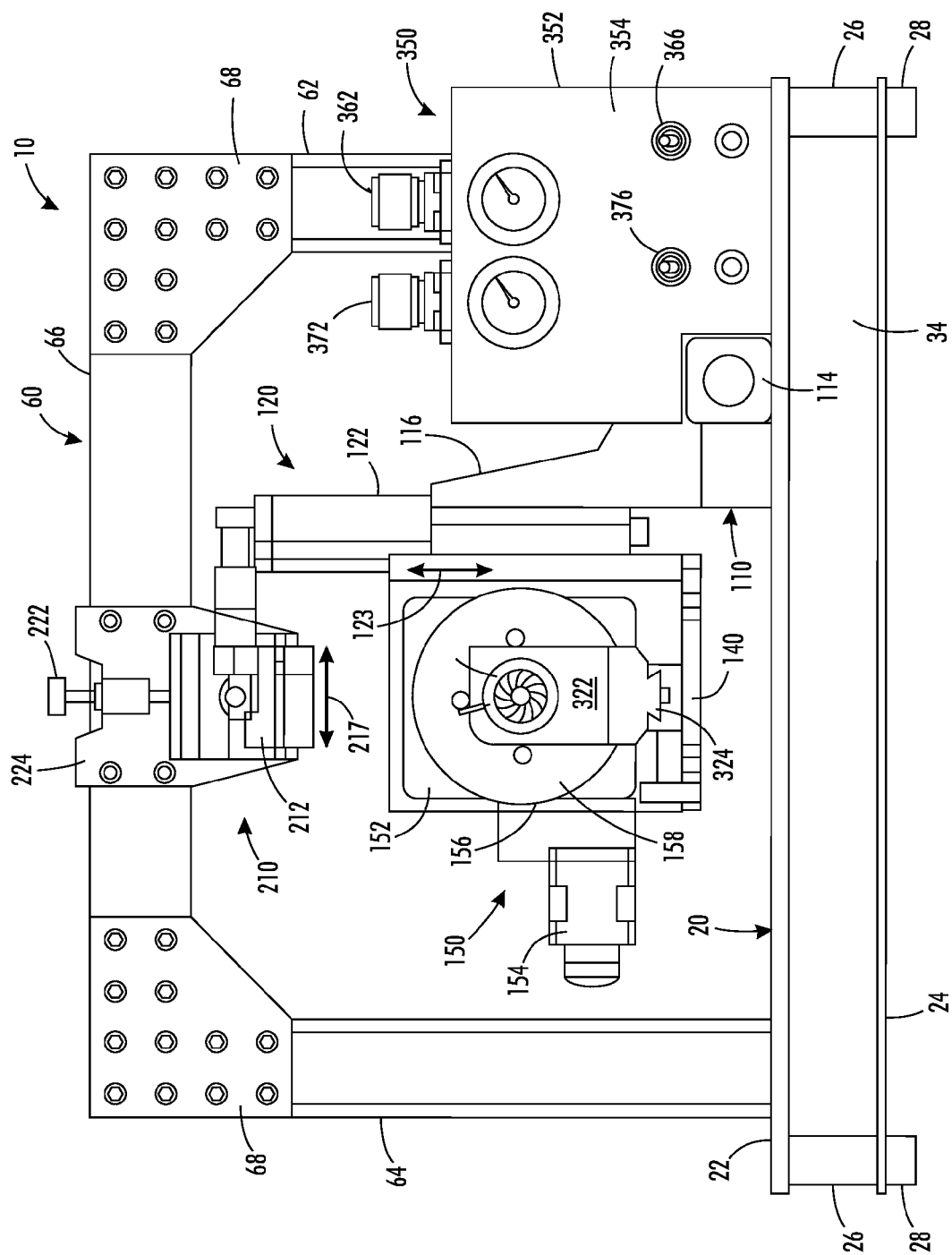
FIG. 3 is a front elevation view of the system of FIG. 2.

Turning first to FIG. 2, the orientation of the x, y, and z axes used in the following description are shown. Referring also to FIGS. 3-9, the scanning system 10 is comprised of a base 20, upon which various other system components are disposed. The base 20 may be comprised of an upper plate 22 and a lower plate 24, which are held separated by a fixed distance by standoffs 26 located at the corners of the plates 22 and 24, as well as at other locations between the plates 22 and 24. The upper and lower plates 22 and 24 may be joined to each other by fasteners which pass through the standoffs. The fasteners may also be used to secure bumpers or foot pads 28 that are made of rubber or another suitable resilient material.

The base may be further comprised of opposed left and right side walls 30 and 32, and front wall 34, which are disposed between the upper and lower plates 22 and 24, and pairs of adjacent standoffs 26. The upper and lower plates 22 and 24, and the side walls 30, 32, and 34 form an enclosure, within which the multi-axis controller 170 may be disposed. This is shown in particular in FIG. 15, in which the lower plate 24 has been removed. The base 20 may be further comprised of a insert 36 that is made of polymer foam, or another suitable lightweight insulative material.

Referring again to FIGS. 2-9, a first support structure 60 is provided for supporting the first probe 200 (FIGS. 11-14) that is used to scan the object 2. In the embodiment depicted in FIGS. 2-9 and FIG. 13, the support structure 60 is provided as a gantry comprised of first and second upright support members 62 and 64 that are joined to the base 20, and a cross support member 66 joined to the upright support members 62 and 64. The support members 62, 64, and 66 may be made of an extruded aluminum shape, and joined by gussets 68, or other suitable means. Such extruded aluminum shapes are preferred because they are formed with channels for fastening objects thereto, and thus provide a convenient means for mounting the first probe 200. However, other structures may be provide that are suitable for supporting the probe 200.

The means 210 for supporting the first probe 200 will now be described, with reference in particular to FIGS. 2-6 and FIG. 13. The probe 200 is mounted in a fixture 212, which is provided with an opening 214 for receiving and gripping the probe 200. In one embodiment, the fixture 212 may be a gimbal mount. The fixture 212 is preferably mounted on a first linear slide 216, which is mounted on a second linear slide 218, which is mounted on the support structure 60. The orientation of the slide motion of the first linear slide 216 is in the z-direction as indicated by bidirectional arrow 217, and the orientation of the slide motion of the second linear slide 218 is in the y-direction as indicated by bidirectional arrow 219. The slide motion of the first linear slide 216 may be adjusted by fine adjustment screw 220, and the slide motion of the second linear slide 218 may be adjusted by fine adjustment screw 222. In that manner, the location of the probe 200 may be adjusted so that it is aligned with the central axis of the object to be scanned; and so that for a cylindrical object, any beam of light emitted in the direction of the central axis of the probe 200 will be perpendicular to the surface of the object to be scanned. The fine adjustment screws 220 and 222 may be micrometer adjustment screws, such as screw 221 of FIG. 13. The second linear slide 218 may be mounted on an intermediate plate 224, which is joined to the cross support member 66.

The first probe 200 is mounted on the first support structure 60, such that it is held stationary, while the multi-axis drive module 100 drives the object 2 linearly and rotationally along the first probe 100 to linearly and rotationally scan the object 2. Aspects of the multi-axis drive module 100 will now be described with reference in particular to FIGS. 2-9, 11, and 12.

The multi-axis drive module 100 is comprised of a first linear drive 110 linearly drivable along a first axis, a second linear drive 120 joined to the first linear drive 110 and linearly drivable along a second axis non-parallel to the first axis, and a first rotary drive 150 mounted on the second linear drive 120. In the embodiment depicted in FIGS. 2-9, 11, and 12, the first linear drive 110 is comprised of a first stage 112 that is linearly drivable along a first axis in the x direction, as indicated by bidirectional arrow 113. The drive 110 is further comprised of a drive motor 114, which may be a stepper motor.

The second linear drive 120 is comprised of a second stage 122, which is joined to the first stage 112 and which is linearly drivable along a second axis in the y direction as indicated by bidirectional arrow 123. The drive 120 is further comprised of a drive motor 124, which also may be a stepper motor. The stage 122 of the second linear drive 120 may be joined to the stage 112 of the first linear drive by use of a first bracket 116, and suitable fasteners which join the surface of the stage 112 to a horizontal bracket plate 117, and which join the surface of the stage 122 to a vertical bracket plate 118. The net result of the linear motion capabilities of the first linear drive 110 and the second linear drive 120 is that the object to be scanned, such as balloon catheter 2 in FIGS. 11 and 12, can be translated linearly with respect to probe 200, as indicated by bidirectional arrows 115 and 125.

Figure 4:
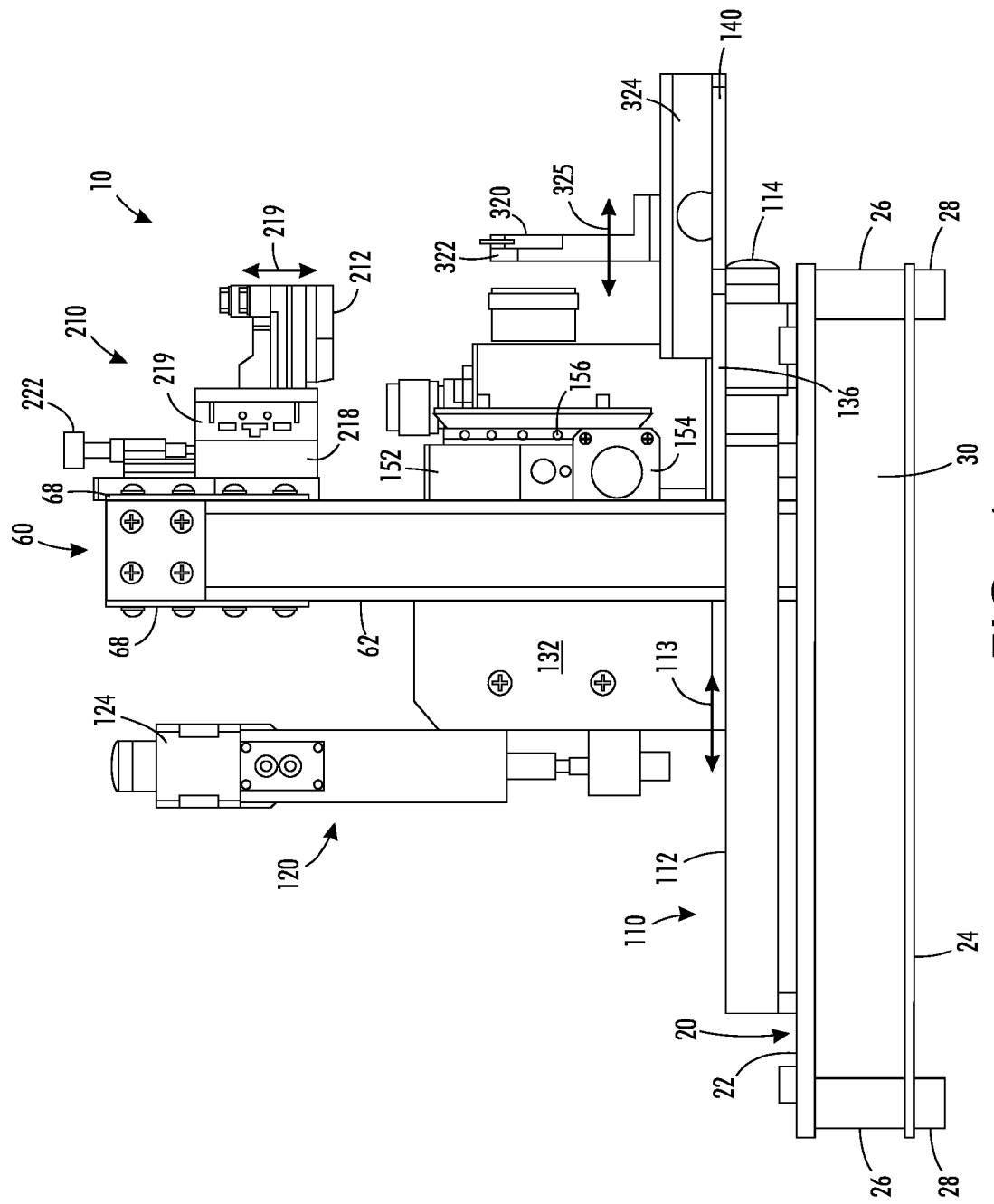
FIG. 4 is a right side elevation view of the system of FIG. 2.
Figure 5:
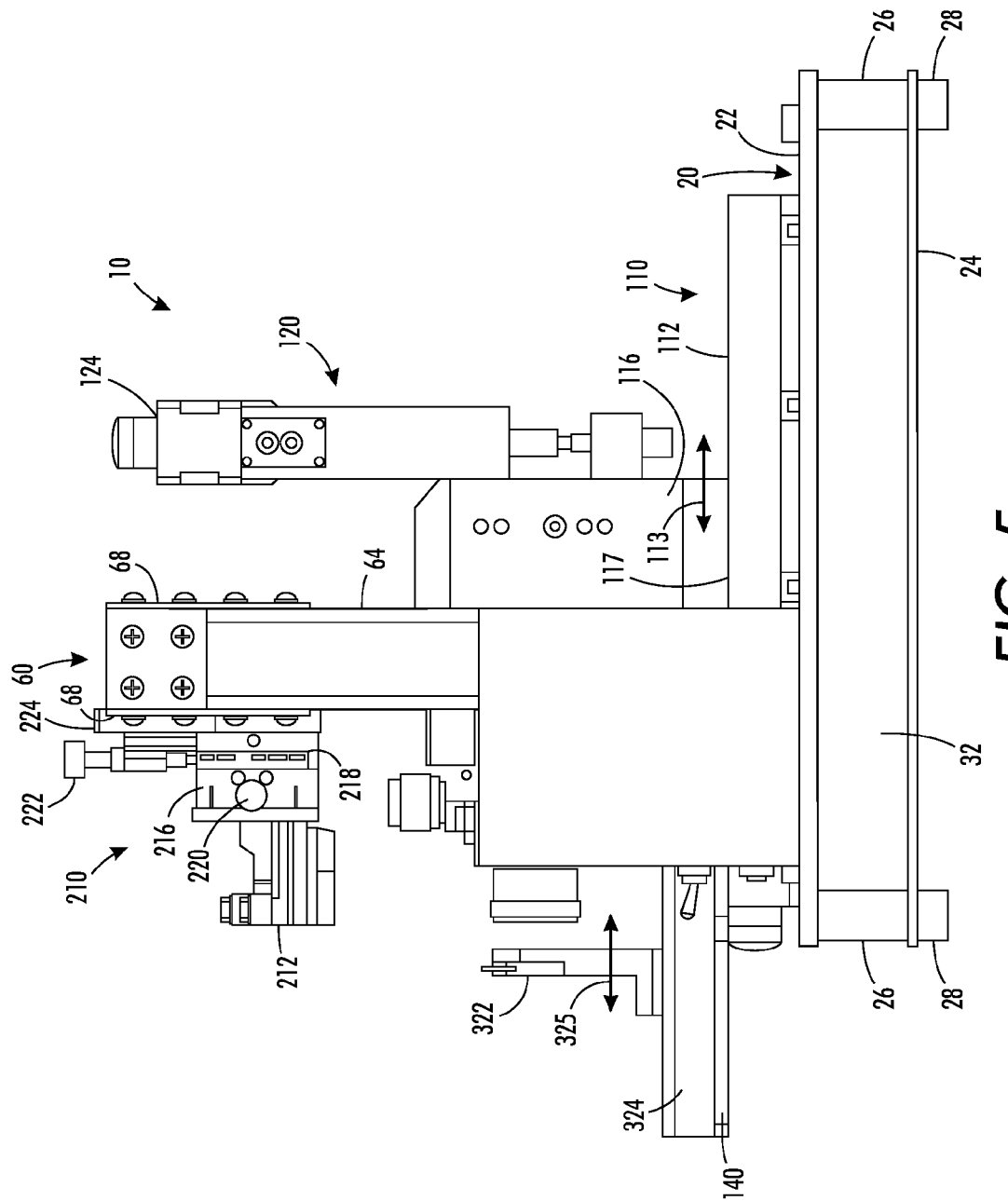
FIG. 5 is a left side elevation view of the system of FIG. 2.
Figure 6:
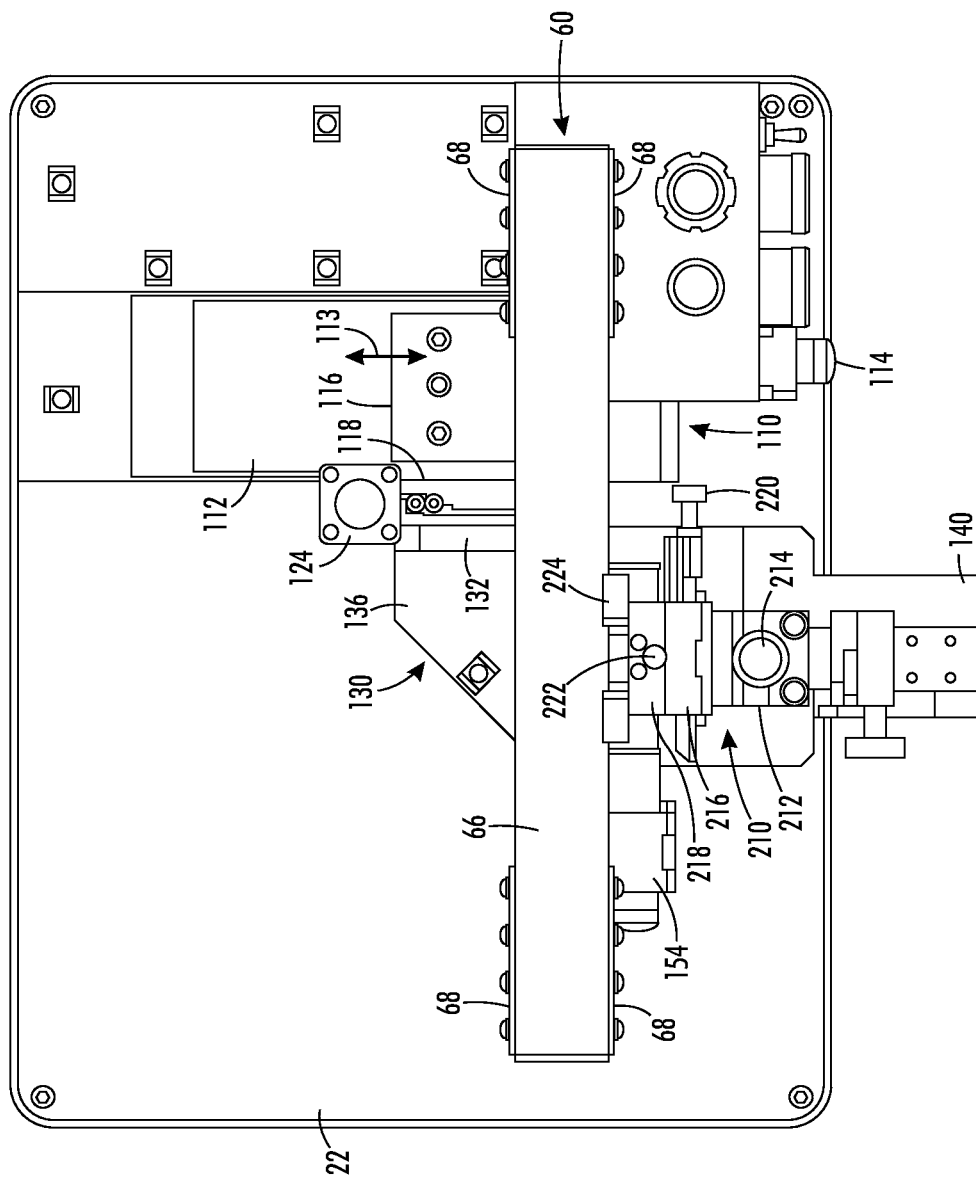
FIG. 6 is a top view of the system of FIG. 2.
Figure 7:
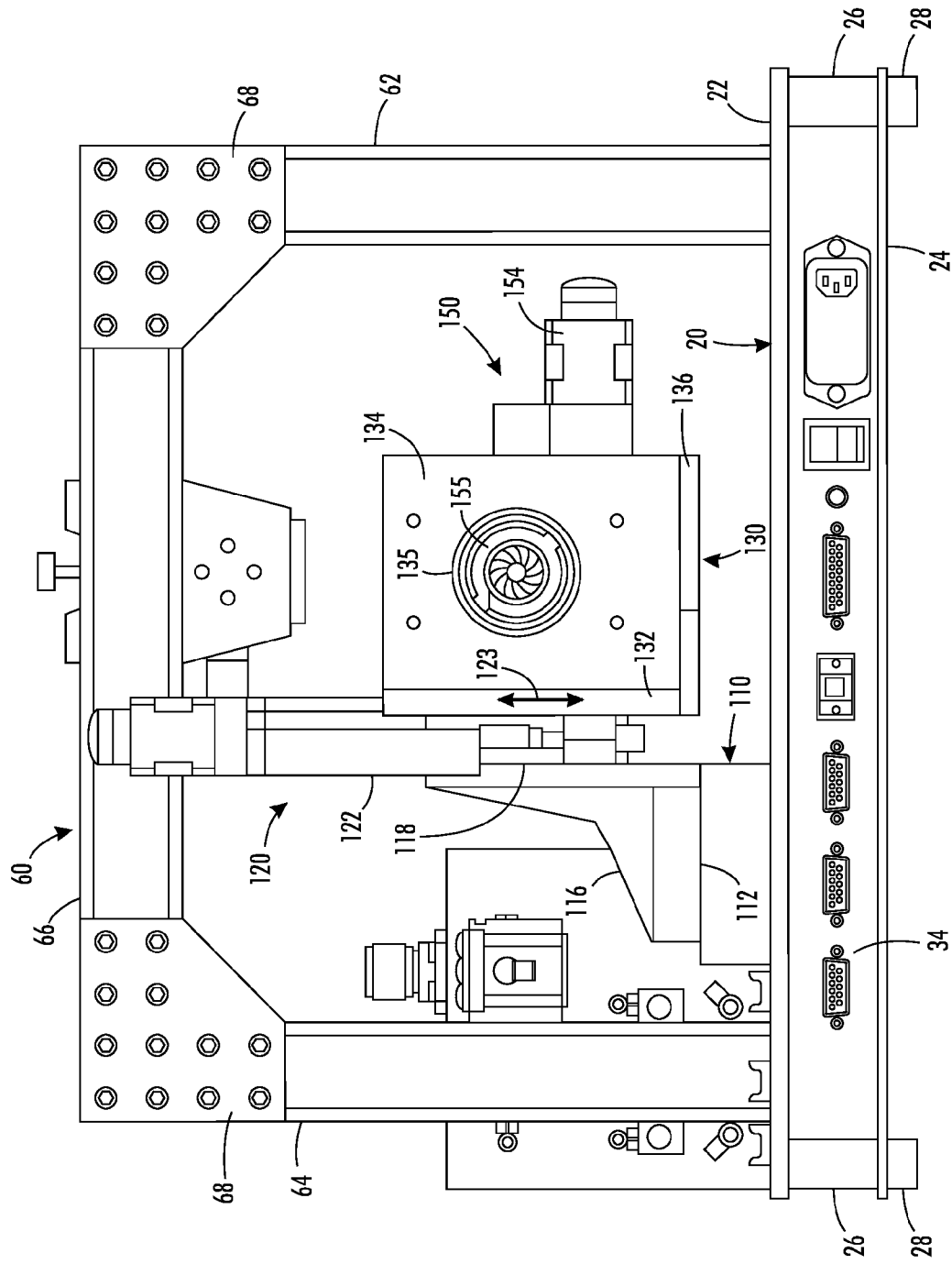
FIG. 7 is a rear elevation view of the system of FIG. 2.
Figure 8:
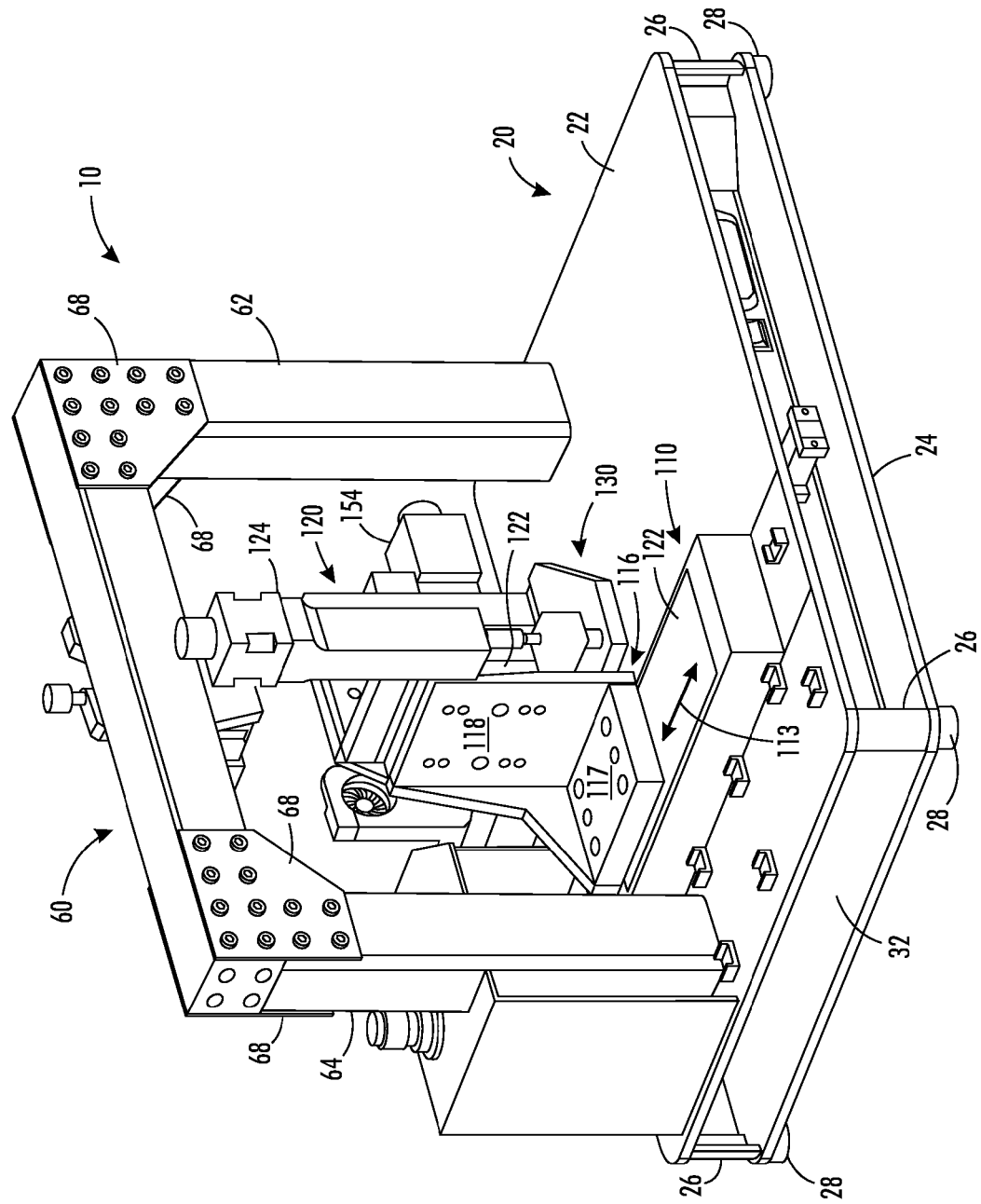
FIG. 8 is a left rear perspective view of the system of FIG. 2.
Figure 9:
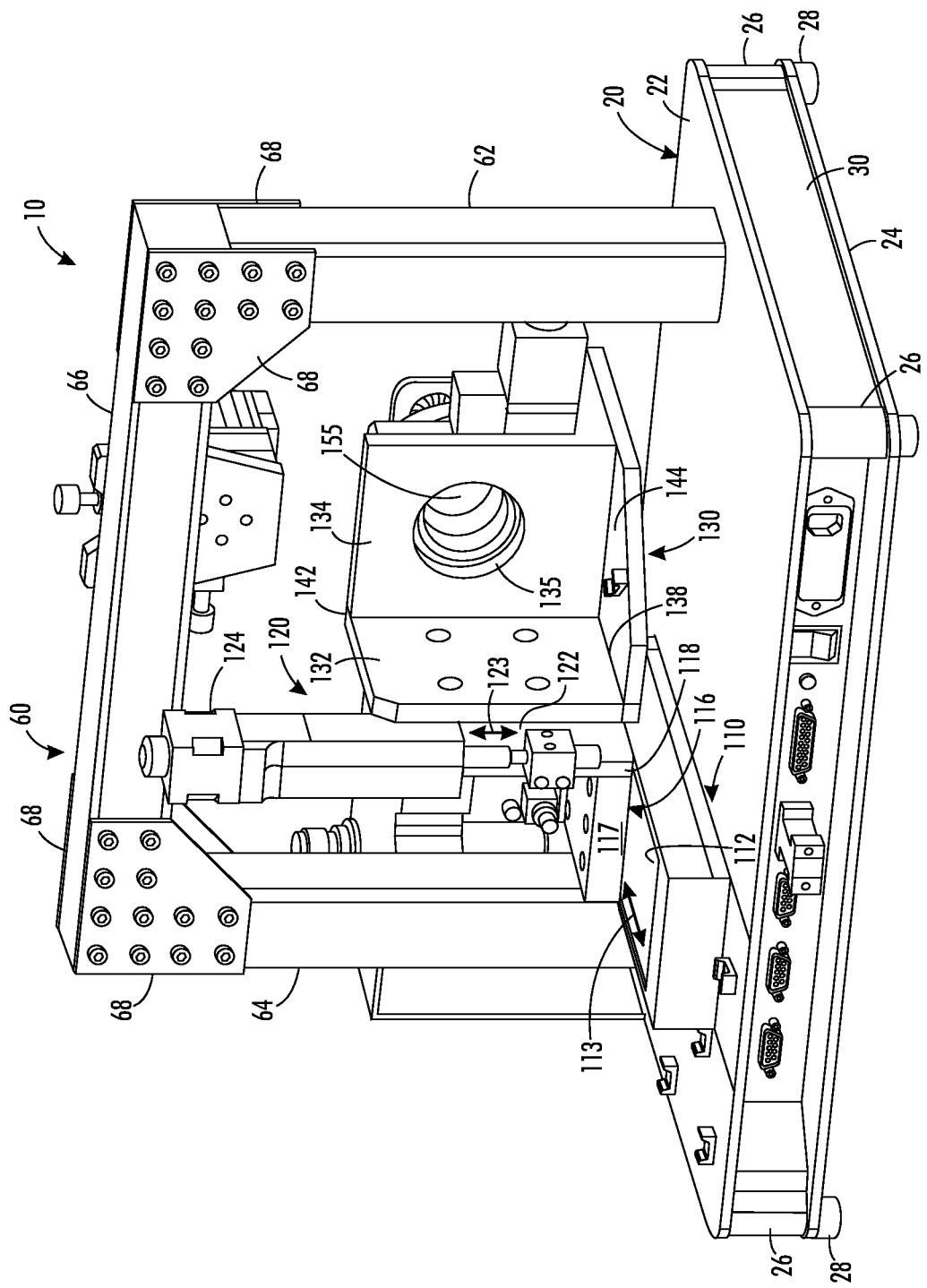
FIG. 9 is a right rear perspective view of the system of FIG. 2.

The rotary drive 150 may be mounted on the second stage 122 using a second bracket 130, which is comprised of a first vertical bracket plate 132, a second vertical bracket plate 134, and a horizontal bracket plate 136 joined to each other by fasteners or other suitable means. Referring in particular to FIGS. 9, 2, and 4, the first vertical bracket plate 132 is oriented in an x-y plane and is joined to the second stage 122. The horizontal bracket plate 136 is oriented in an x-z plane, and is joined to the lower end 138 of the first vertical bracket plate. The horizontal bracket plate 136 is comprised of a forwardly extending region 140, which provides a structure for mounting one or more outward supports for the object to be scanned as will be explained subsequently herein. The second vertical bracket plate 134 is oriented in a y-z plane, and is joined to the side 142 of the first vertical bracket plate, and to the top surface 144 of the horizontal bracket plate 136.

The rotary drive 150 is comprised of a drive housing 152 that is joined to the forward surface 146 of the second vertical bracket plate 134, a drive motor 154, and a rotary stage 156. The drive motor 154 may be a stepper motor. The rotary stage 156 is rotatable around an axis oriented in the x-direction as indicated by arcuate arrow 157.

Figure 10A:
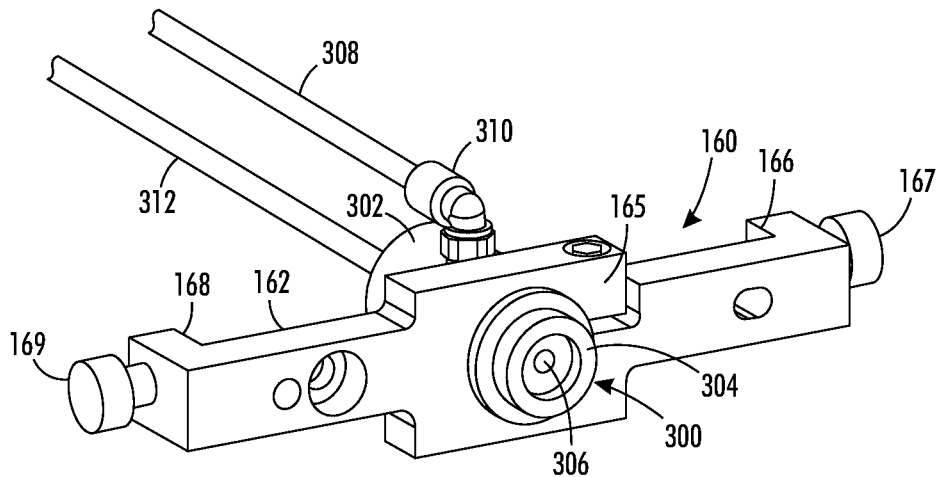
FIG. 10A is a front perspective view of a collet that is attachable to a spindle of the system of FIG. 2 for holding and rotating a balloon catheter or other object during scanning.
Figure 10B:
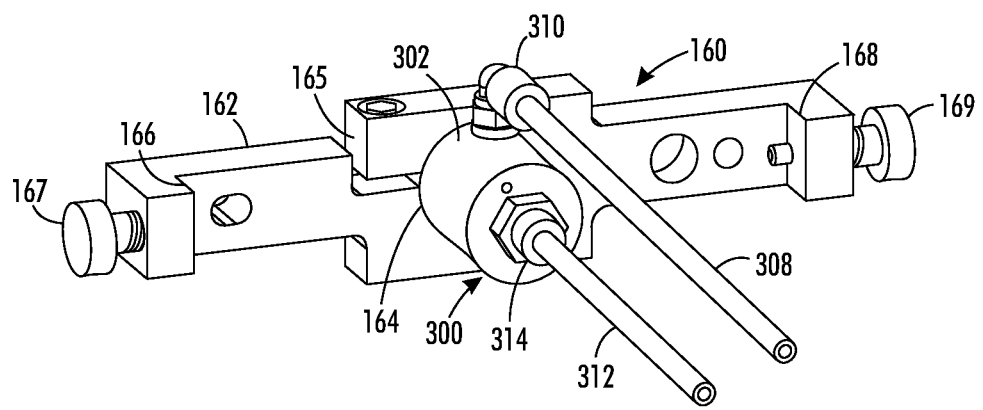
FIG. 10B is a rear perspective view of the collet of FIG. 10A.
Figure 11:
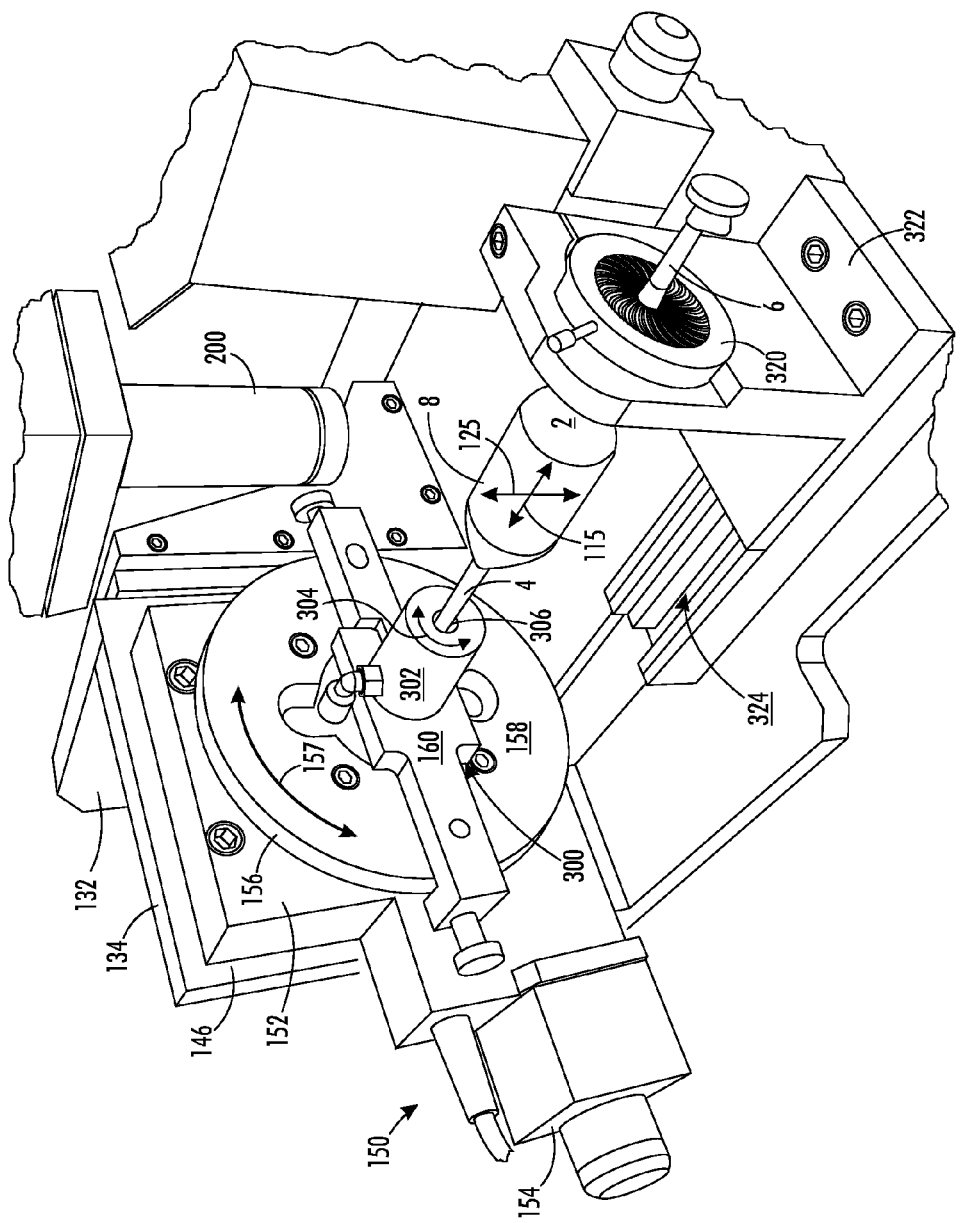
FIG. 11 is a front perspective view of rotary drive fixture for holding a balloon catheter or other object to be scanned, along with a first optical probe.

The rotary stage 156 is further comprised of a rotary fixture for holding the object 2 to be scanned. When the object 2 is held by the rotary fixture, it may be rotated while the first probe 200 is scanned along the object 200 in the x-direction. In that manner, the object may be linearly and rotationally scanned by the system 10. Referring in particular to FIGS. 2, 3, 11, and 12, the rotary fixture may be comprised of a rotary plate 158, a collet fixture 160 that is removably joined to the rotary plate 158, and a rotary collet 300 held by the collet fixture 160. Referring also to FIGS. 10A and 10B, the collet fixture 160 may be comprised of an elongated bar 162 having a central through bore 164 for receiving the collet 300, and a split clamp 165 for firmly holding the collet 300. The elongated bar 162 may be further comprised of opposed end shoulders 166 and 168, within which are disposed opposed thumb screws 167 and 169. When the collet fixture 160 is fitted to the rotary plate 158, the opposed end shoulders 166 and 168 extend rearwardly along the outer edge of the rotary plate 158, so that the thumb screws 167 and 169 may be turned inwardly against the rotary plate 158, thereby securing the collet fixture 300 to the rotary plate 158. The rotary plate 158 may be provided with a pair of dowel pins, and the elongated bar 162 may be provided with a pair of corresponding holes therein, located so as to precisely align the central through bore 164 of the collet fixture 160 with the axis of rotation of the rotary stage 156 and plate 158.

The rotary collet 300 is comprised of a collet body 302 having an outboard end 304 with a central object-receiving port 306. When the object to be scanned is comprised of an elongated cylinder at a proximal end of the object, such as the proximal end tubing 4 of the balloon catheter 2 in FIGS. 11 and 12, the elongated cylinder (e.g., tubing 4) is received in the central object-receiving port 306. The rotary collet 300 may be further comprised of a gripper for gripping the elongated cylinder that is received in the port 306. The gripper may be hand operated, or the gripper may be electrically and/or mechanically operated. In the embodiment depicted in FIGS. 10A-12, the rotary collet 300 is comprised of a pneumatic gripper (not shown) that is contained within the collet body 302. A pneumatic signal (e.g., pressurized air) is supplied to the pneumatic gripper through a conduit 308 and a fitting 310 that is disposed in the collet body 302.

Additionally, for the purpose of scanning objects that have an internal cavity, the system 10 may be comprised of means for pressurizing the internal cavity of the object to stabilize a first region of the object. In one embodiment, such means may be a hydraulic or pneumatic circuit. For a pneumatic circuit, a pneumatic signal may be supplied to the central port 306 through a conduit 312 and a fitting 314 that is disposed in the inboard end 316 of the collet body 302. In that manner, the pneumatic signal may be used to provide pressurized air (or another gas) to the internal cavity of the object. Where the object is a balloon catheter 2, the pneumatic signal is used to inflate the balloon during the scanning process, thereby providing a taut, uniform surface for scanning. In other words, by pressurizing the object with a fluid introduced into a cavity therein, a region of the object to be scanned, such as the central region 8 of the balloon catheter 2 (FIG. 11), is dimensionally stabilized.

In such an embodiment, the system 10 may be further comprised of a pneumatic module 350 for operating the pneumatic collet 300. Referring in particular to FIGS. 1-3, 10A, 10B, and 13, the pneumatic module 350 is comprised of a first pneumatic circuit 370 in communication with the central object-receiving port 306 of the rotary collet 300, and a second pneumatic circuit 360 in communication with the pneumatic gripper, so as to actuate and release the gripping action of the gripper on the object 2. The pneumatic circuits 360 and 370 may be contained within an enclosure 352 comprising a front panel face 354. The first pneumatic circuit 370 may be comprised of a first regulator 372, and a first on-off valve 374 operated by a first toggle 376 disposed in panel face 354. The second pneumatic circuit 360 may be comprised of a second regulator 362 for varying the pressure provided to the internal cavity of the object, and a second on-off valve 364 operated by a second toggle 366 disposed in panel face 354.

The first pneumatic circuit 370 is connected to the central port 306 in the rotary collet 300 through conduit 312, and the second pneumatic circuit 360 is connected to the gripper in the rotary collet 300 through conduit 308. The conduits 308 and 312 pass rearwardly through a central opening 155 in the rotary plate 158 and the drive housing 152, and then through an opening 135 (FIG. 9) in the second vertical plate 134 of the second bracket 130, and then to the pneumatic enclosure 352. Conduits 308 and 312 are preferably formed of thin, flexible tubing, so that during scanning of an object, the rotary stage 156 can be rotated at least several turns in either direction. During such rotation, the flexible conduits 308 and 312 become entwined or braided with each other, and become unbraided when the rotational direction is reversed.

The object 2 to be scanned may be supported by additional means other than the collet 300. The system 10 may be provided with one or more additional support structures for supporting the outboard end of the object 2. Referring in particular to FIGS. 2-5 and 11-14, a first aperture 320 is provided to support the distal end 6 (FIG. 11) or the central region 8 (FIG. 14) of the object 2. The aperture 320 may be a variable diameter iris-like aperture, such as is used in optical shutters, so as to accommodate objects of different diameters, or sections of the object having different diameters. The aperture 320 may be mounted on a bracket 322, which may be mounted on a linear slide 324, which in turn is disposed on the forwardly extending region 140 of the bracket plate 136. The linear slide 324 is oriented to provide adjustment of the location of the aperture 320 in the x-direction as indicated by bidirectional arrow 325, so as to enable the aperture 320 to be positioned at a desired location for support of the object 2. In one embodiment depicted in FIG. 13, a second aperture 330 and bracket 332 may be provided upon slide 324.

Referring again to FIGS. 1, 2, and 15, the multi-axis drive module 100 may be further comprised of a multi-axis controller 170 in signal communication with the first linear drive 110, the second linear drive 120, and the first rotary drive 150. The multi-axis controller 170 may be disposed in an enclosure formed between the upper and lower plates 22 and 24 of the base 20. The rear wall 38 between the upper and lower plates 22 and 24 may be provided with cable connections 172, 174, 176, and 177 for cables (not shown) to the first linear drive 110, the second linear drive 120, the first rotary drive 150, and an additional input device (not shown) such as a joystick; a USB port 178 for communication with the controller 170; and ON/OFF switch 180 for the controller 170; and a connection 182 for power supply to the controller 170 and the drives 110, 120, and 150.

Figure 12:
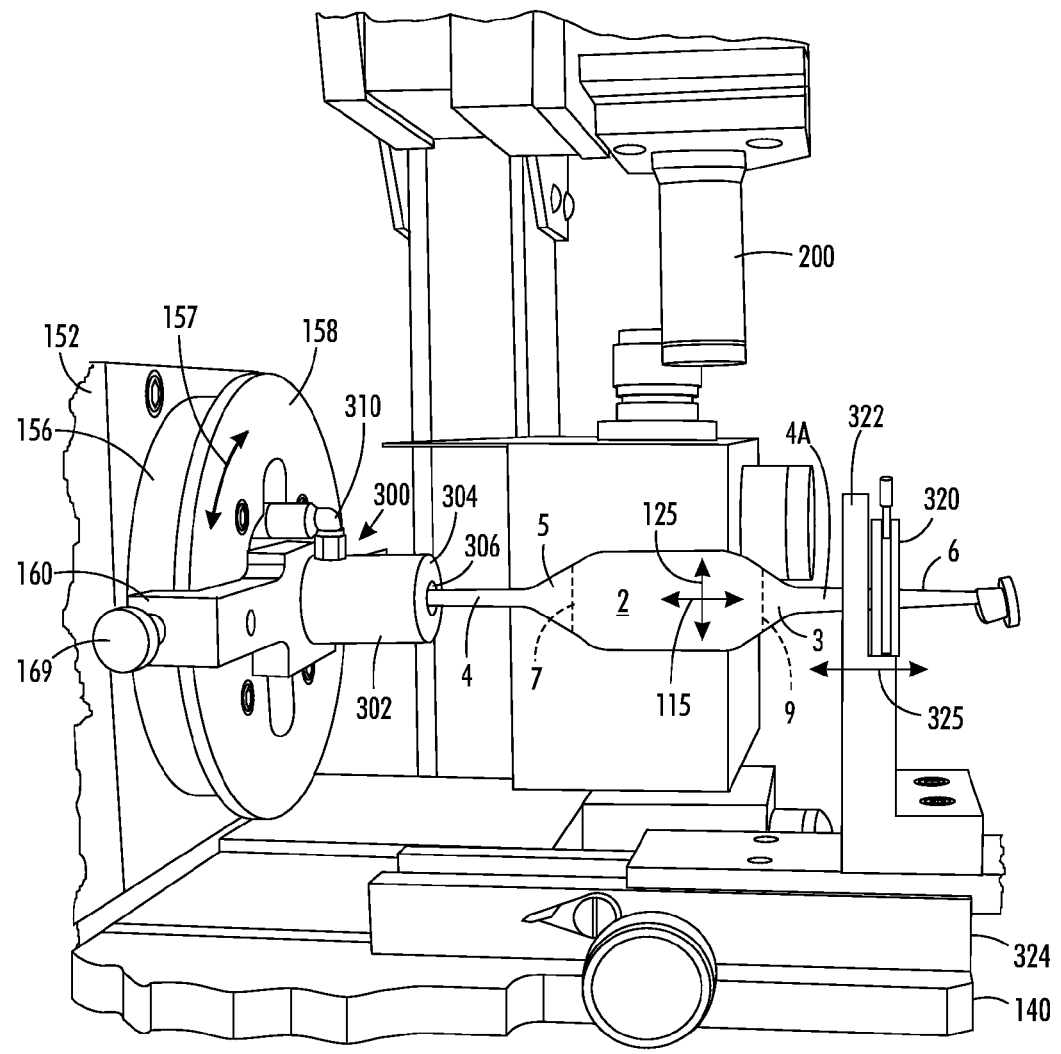
FIG. 12 is a side elevation view of the fixture, optical probe, and balloon catheter of FIG. 11.
Figure 13:
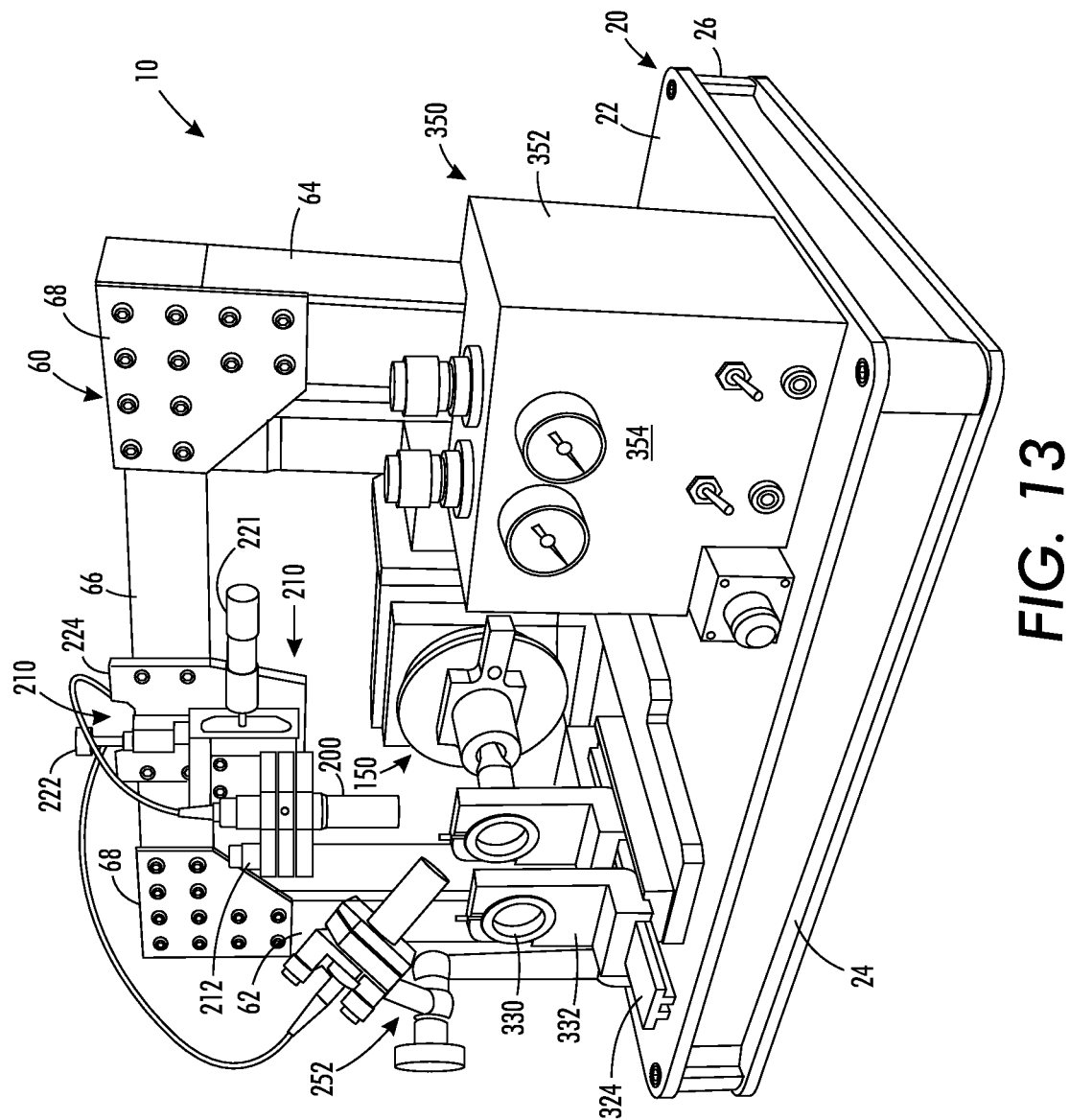
FIG. 13 is a front perspective view of another embodiment of the rotational and linear scanning system comprising two optical probes.
Figure 14:
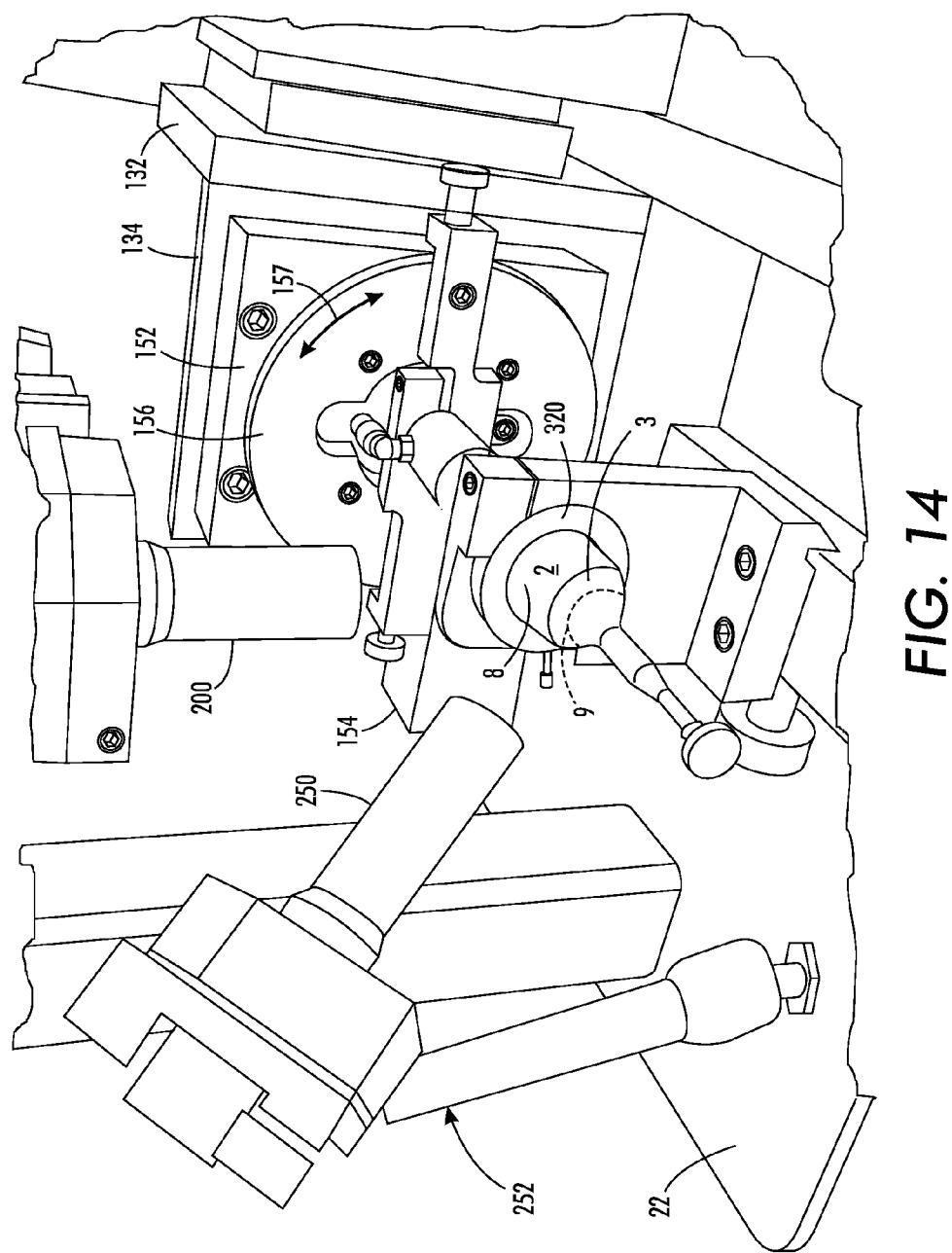
FIG. 14 is a detailed front perspective view of the optical probes of the system of FIG. 13, shown aligned and ready to measure a balloon catheter.
Figure 15:
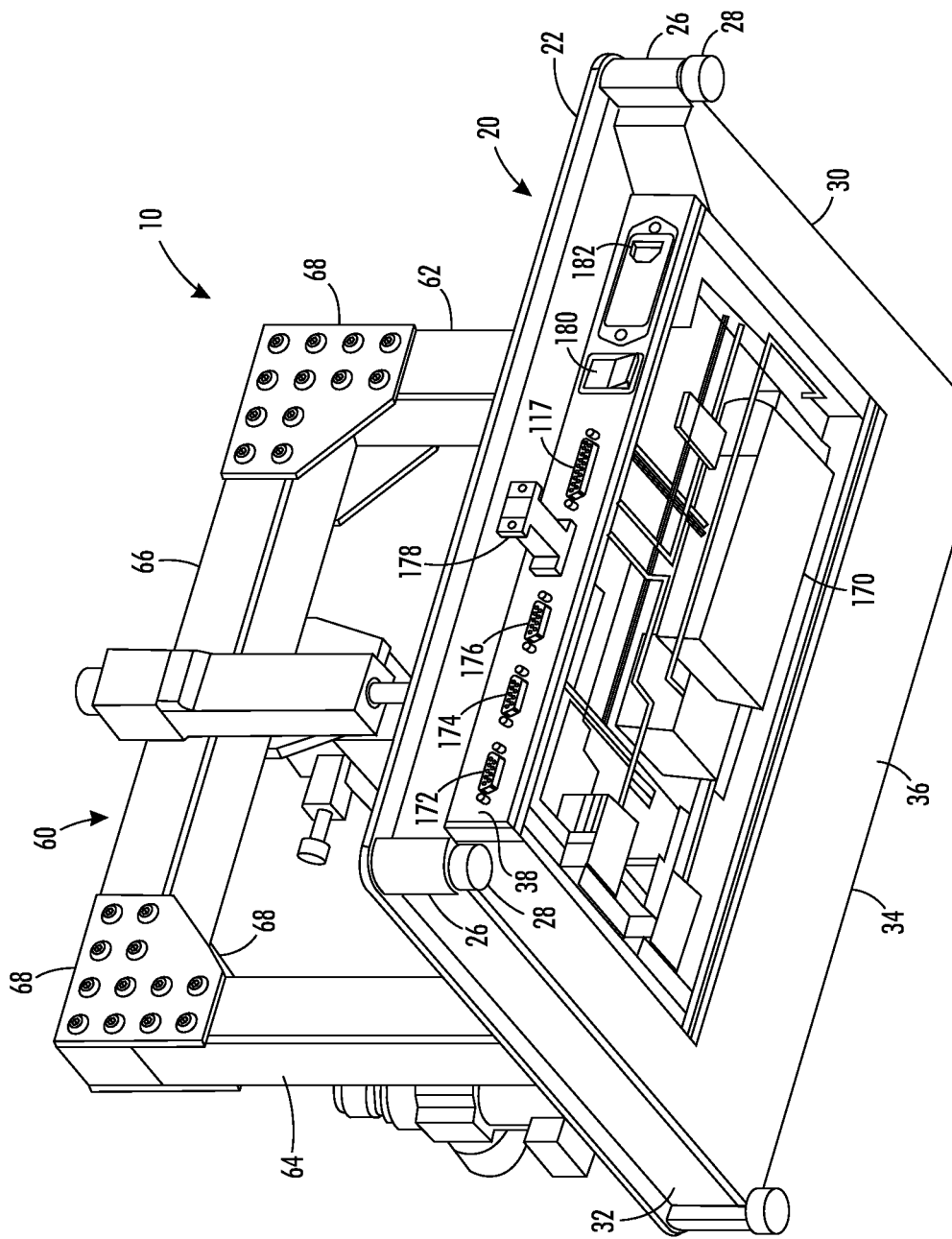
FIG. 15 is a lower rear perspective view of a rotational and linear scanning system.

The system 10 may be further comprised of a second probe 250 mounted on the base 20, and alignable with at least a portion of the object to be scanned. This feature is particularly useful for scanning the conically tapered end regions 3 and 5 (FIG. 12) of the balloon catheter 2. Referring in particular to FIGS. 13 and 14, a second probe 250 is shown mounted on an articulating arm assembly 252, which is joined to the upper plate 22 of the base 20. The probe 250 is positioned so as to scan a circle 9 of the outer conical region 3 of the catheter 2, with the central axis of the probe 250 being substantially perpendicular to the surface of the catheter along the circle 9. The probe 250 is manually positionable to also scan a circle 7 of the inner conical region 3 of the catheter 2 (FIG. 12). In a further embodiment (not shown) the manually articulating arm 252 may be replaced with a robotic arm, which can be programmed to move the probe 250 to different regions of the object to be scanned, such as conical regions 3 and 5.

The probes 200 and 250 of the system 10 may be optical probes. In one embodiment, the probes 250 are interferometric optical probes as described in the aforementioned United States patents of Marcus et al., which are incorporated herein by reference. Such interferometric optical probes, as well as a system for acquiring and processing data obtained to determine object diameters and layer/film thicknesses is manufactures and sold as the OptiGauge™, by Lumetrics, Inc. of West Henrietta N.Y.

In other embodiments, either of the probes 200 and 250 may be a camera for acquiring images of the object 2. The camera may be a vision system camera, the images from which may be analyzed and used by the multi-axis drive module 100 to control the scanning of the object 2. In the embodiment in which probe 200 is a camera, images may be captured while the pressure to the cavity of the object 2 is varied.

Referring again to FIG. 1, the system 10 may be further comprised of a computer 400 in signal communication with the multi-axis drive module 100 and with the first and second probes 200 and 250. The communication with the multi-axis drive module 170 may be provided through the USB port 178, such that a programmed sequence for a linear and rotational scan of an object may be uploaded to the drive module 170, and then executed by the linear drives 110 and 120, and the rotary drive 150.

The system 10 may further include a signal converter 430 in signal communication with the computer 400 and with the first probe 200 and second probe 250. In an embodiment in which the probes 200 and 250 are optical probes, the probes 200 and 250 may be in communication with the signal converter 430 through fiber optics 204 and 254, with the signal converter processing the optical signals from the probes 200 and 250 into electrical signals to the computer 400. In an embodiment in which the optical probes are interferometric probes, the signal converter 430 may be a converter as supplied with the OptiGauge™ system by Lumetrics, Inc. The computer 400 may include a screen display 402 for displaying scanning results, input devices such as a mouse and/or keyboard (not shown), a central processing unit (not shown), a memory (not shown), and at least one storage medium such as a hard disk (not shown) for storing scanning results.

Figure 16:
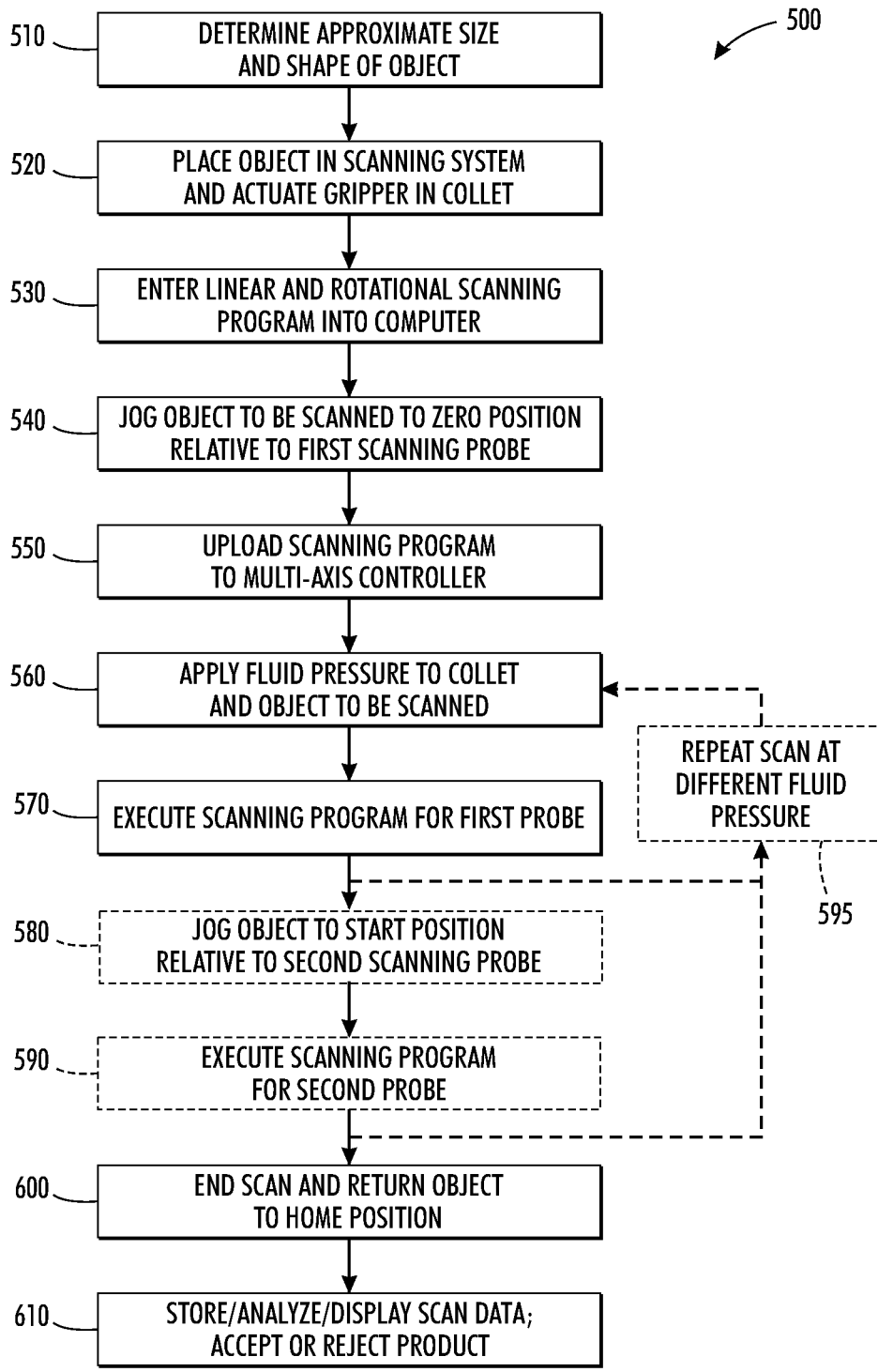
FIG. 16 is a flowchart of methods of scanning an object using the rotational and linear scanning system.

FIG. 16 is a flowchart of a method 500 of scanning an object using the rotational and linear scanning system 10. Prior to performing a scan, the approximate dimensions and shape of the object are determined in step 510, in order to prepare a recipe or scanning program to be executed. These dimensions provide the regions of substantially constant diameter of the object that may be scanned with the first probe 200, and regions of varying diameter that may be scanned with the second probe 250. For example, the central region 8, the proximal end tubing region 4, and the distal end tubing region 4A of the balloon catheter 2 of FIG. 12 are regions of substantially constant diameter; and the conical regions 3 and 5 are regions of varying diameter. In step 520, the catheter 2 is placed in the collet 300 and the gripper is actuated. In step 530, a scanning program for movement of the catheter 2 relative to the probe 200 and probe 250 is entered into the computer 400 and stored. The position of the catheter 2 relative to the probe 200 and probe 250 may be jogged to a desired "zero" starting position in step 540. The measurement system including probes 200 and optionally probe 250 is placed on-line and ready to scan.

In step 550, the computer 400 then uploads the program to the multi-axis controller 170. The balloon is pressurized with fluid in step 560, and the scanning program for the first probe 200 is executed in step 570. The catheter 2 is moved linearly beneath the first probe 200 continuously or in increments by the first linear drive 110, thereby scanning a first region of the catheter 2. Simultaneously, the catheter 2 may be rotated continuously or in increments by the rotary drive 150. When a transition to a region of different diameter, such as conical region 3 is reached during the scan, the second linear drive

120 may be actuated to adjust the distance between the surface of the catheter 2 and the end of the probe 200, in order to maintain the desired scanning distance between them. The scan may continue along a second region such as the central region 8 of the catheter 2, and then the second linear drive 120 may again adjust the position of the catheter 2 relative to the probe 200, and linear scanning with rotation may be continued. When the linear scanning with probe 200 is complete, the first and second linear drives 110 and 120 may be actuated to position the catheter such that the second probe 250 is aligned with a third region of the catheter 2, such as conical region 3 in step 580. The catheter 2 is rotated by the rotary drive 150 while a rotational scan of the conical region 3 is performed in step 590.

The scan may be repeated multiple times at different balloon fluid pressures in steps 595 after a scan with the first probe 200 and/or the second probe 250. Or the scan may then be completed, with the catheter 2 moved to the original starting position, or another end position in step 600. During the entire scanning process, the computer 400, optionally using the signal converter 430, is acquiring and storing scanning data of the object, such as outside diameter and layer thickness data. The data may be loaded into a spreadsheet or a database, and/or plotted graphically and displayed on the screen 402, and/or compared to specifications, with an indication of "accept" or "reject" of the catheter 2 or other object in step 610.

It is, therefore, apparent that there has been provided, in accordance with the present invention, a method and apparatus for performing rotational and linear scanning of objects. Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefor, is not intended to limit the claimed processes to any order except as may be specified in the claims.

We claim:

1. A method for determining the wall thickness of an object comprising a wall surrounding an internal cavity and defining an exterior surface, the method comprising:
   a) gripping the object;
   b) connecting the internal cavity to a source of fluid;
   c) delivering fluid into the internal cavity to cause a first pressure difference between the internal cavity and the exterior surface of the object;
   d) scanning a first portion of a first region of the object with a first low coherence interferometric optical probe to obtain interferometric data; and
   e) using the interferometric data to compute the wall thickness of the object as a function of position over the first portion of the first region of the object.

2. The method of claim 1, further comprising rotating the object, and scanning a second portion of the first region of the object with the first low coherence interferometric optical probe and determining the wall thickness of the object as a function of position over the second portion of the first region of the object.

3. The method of claim 1, further comprising rotating the object, and scanning a first portion of a second region of the object with a second low coherence interferometric optical probe and determining the wall thickness of the object as a function of position over the first portion of the second region of the object.

4. The method of claim 1, further comprising causing a second pressure difference between the internal cavity and the exterior surface of the object, and scanning the first region of the object with the first low coherence interferometric optical probe.

5. A system for determining the wall thickness of an object having axial symmetry and comprising a wall surrounding an internal cavity and defining an exterior surface, the system comprising:
   a) means for gripping the object;
   b) means for delivering fluid into the internal cavity of the object to cause a pressure difference between the internal cavity and the exterior surface of the object; and
   c) a first low coherence interferometric optical probe and means for scanning the first low coherence interferometric optical probe linearly and circumferentially relative to a first region of the object.

6. The system of claim 5, further comprising a second low coherence interferometric optical probe, and means for scanning the second low coherence interferometric optical probe circumferentially relative to a second region of the object.

7. The system of claim 5, further comprising means for varying the pressure provided to the internal cavity of the object.

8. The method of claim 1, wherein the delivering fluid into the internal cavity to cause a pressure difference between the internal cavity and the exterior surface of the object causes the wall of the object to be dimensionally stabilized.

9. The method of claim 3, wherein the object is axially symmetric, the first region of the object is of a constant diameter, and the second region of the object is of a varying diameter.

10. A method for determining wall thickness of an object and at least one other physical property of the object as a function of position on the object, the object comprising a wall surrounding an internal cavity and defining an exterior surface, and the method comprising:
    a) gripping the object;
    b) delivering fluid into the internal cavity of the object to cause a first pressure difference between the internal cavity and the exterior surface of the object;
    c) scanning a first portion of the first region of the wall of the object with a first low coherence interferometric optical probe to obtain interferometric data; and
    d) using the interferometric data from the first low coherence interferometric optical probe to determine the wall thickness and the at least one other physical property of the object as a function of position over the first portion of the first region of the wall of the object.

11. The method of claim 10, further comprising rotating the object, and scanning a second portion of the first region of the wall of the object with the first low coherence interferometric optical probe and using interferometric data from the first low coherence interferometric optical probe to determine the wall thickness and the at least one other physical property of the object as a function of position over the second portion of the first region of the object.

12. The method of claim 10, further comprising rotating the object, and scanning a first portion of a second region of the object with a second low coherence interferometric optical probe and using interferometric data from the second low coherence interferometric optical probe to determine the wall thickness and the at least one other physical property of the object as a function of position over the first portion of the second region of the object.

13. The method of claim 10, further comprising causing a second pressure difference between the internal cavity and the exterior surface of the object, and scanning the first region of the object with the first low coherence interferometric optical probe.

14. The method of claim 10 wherein the at least one other physical property of the object includes at least one of individual layer thickness, outside diameter, ovality, concentricity and inside diameter.

15. The method of claim 10 wherein the low coherence interferometric optical probe is coupled to a low coherence interferometer comprising a low coherence light source that directs low coherence light to the object.

16. The method of claim 10 wherein the object is one of a transparent, translucent, or colored object.

17. The method of claim 10 wherein the object is a balloon catheter.

18. A system for determining wall thickness and at least one other physical property of an object having axial symmetry as a function of position over a first region of the object, the object comprising a wall surrounding an internal cavity and defining an exterior surface, and the system comprising:
   a) a gripper for gripping the object;
   b) means for delivering fluid into the internal cavity of the object to cause a pressure difference between the internal cavity and the exterior surface of the object, thereby stabilizing the first region of the object;
   c) a first low coherence interferometric optical probe;
   d) a scanner for scanning the first low coherence interferometric optical probe at least one of linearly and circumferentially relative to the first region of the object; and
   e) an analyzer to analyze interferometric data from the first low coherence interferometric optical probe to determine the wall thickness and the at least one other physical property of the object as a function of position over the first region of the object.

19. The system of claim 18, further comprising a second low coherence interferometric optical probe, wherein the scanner scans the second low coherence interferometric optical probe at least one of linearly and circumferentially relative to a second region of the object and the analyzer analyzes interferometric data from the second low coherence interferometric optical probe to determine the wall thickness and the at least one other physical property of the object as a function of position over the second region of the object.

20. The system of claim 19 wherein the second low coherence interferometric optical probe is coupled to a low coherence interferometer comprising a low coherence light source that directs low coherence light to the object.

21. The system of claim 18, further comprising means for varying the pressure difference between the internal cavity and the exterior surface of the object.

22. The system of claim 18 wherein the at least one other physical property of the object includes at least one of individual layer thickness, outside diameter, ovality, concentricity and inside diameter.

23. The system of claim 18 wherein the first low coherence interferometric optical probe is coupled to a low coherence interferometer comprising a low coherence light source that directs low coherence light to the object.

24. The system of claim 18 wherein the object is one of a transparent, translucent, or colored object.

25. The system of claim 18 wherein the object is a balloon catheter.

26. The system of claim 18, where the object is comprised of at least two layers of different materials and the at least one physical property of the object includes individual layer thickness of the at least two layers.

27. The method of claim 10 where the object is comprised of at least two layers of different materials and the at least one physical property of the object includes individual layer thickness of the at least two layers.

* * * * *